United States Patent
Thrope et al.

(10) Patent No.: US 7,376,467 B2
(45) Date of Patent: May 20, 2008

(54) PORTABLE ASSEMBLIES, SYSTEMS AND METHODS FOR PROVIDING FUNCTIONAL OR THERAPEUTIC NEUROMUSCULAR STIMULATION

(75) Inventors: Geoffrey B. Thrope, Shaker Heights, OH (US); Robert B. Strother, Willoughby Hills, OH (US); Joseph J. Mrva, Willoughby Hills, OH (US)

(73) Assignee: NDI Medical, Inc., Cleveland, OH (US)

( * ) Notice: Subject to any disclaimer, the term of this patent is extended or adjusted under 35 U.S.C. 154(b) by 58 days.

(21) Appl. No.: 11/056,591

(22) Filed: Feb. 11, 2005

(65) Prior Publication Data

US 2005/0182457 A1  Aug. 18, 2005

Related U.S. Application Data

(63) Continuation-in-part of application No. 10/777,771, filed on Feb. 12, 2004, now Pat. No. 7,120,499.

(60) Provisional application No. 60/551,945, filed on Mar. 10, 2004, provisional application No. 60/599,193, filed on Aug. 5, 2004.

(51) Int. Cl.
 *A61N 1/18* (2006.01)
(52) U.S. Cl. ............................ 607/48; 607/46; 607/50; 607/115; 607/149
(58) Field of Classification Search ................ 607/149, 607/115, 46, 48, 50
 See application file for complete search history.

(56) References Cited

U.S. PATENT DOCUMENTS

| | | | |
|---|---|---|---|
| 3,939,841 A | | 2/1976 | Dohring |
| 3,943,932 A | | 3/1976 | Woo |
| 4,398,545 A | | 8/1983 | Wilson |
| 4,512,351 A | * | 4/1985 | Pohndorf ............... 607/117 |
| 5,397,338 A | * | 3/1995 | Grey et al. ............. 607/115 |
| 5,449,378 A | | 9/1995 | Schouenborg |
| 5,549,655 A | | 8/1996 | Erickson |
| 5,607,461 A | | 3/1997 | Lathrop |

(Continued)

FOREIGN PATENT DOCUMENTS

JP  2001-190696  7/2001

(Continued)

OTHER PUBLICATIONS

NeuroControl Corporation, NeuroControl St1M System brochure, 2000.

(Continued)

*Primary Examiner*—Carl Layno
*Assistant Examiner*—Natasha Patel
(74) *Attorney, Agent, or Firm*—Ryan Kromholz & Manion, S.C.

(57) ABSTRACT

Neuromuscular stimulation assemblies, systems, and methods make possible the providing of short-term therapy or diagnostic testing by providing electrical connections between muscles or nerves inside the body and stimulus generators or recording instruments mounted on the surface of the skin outside the body. Neuromuscular stimulation assemblies, systems, and methods may include a steerable introducer that defines an interior lumen sized and configured to shield a percutaneous electrode from contact with tissue during advancement to a desired position within tissue.

15 Claims, 11 Drawing Sheets

U.S. PATENT DOCUMENTS

| | | | |
|---|---|---|---|
| 5,857,968 A | 1/1999 | Benja-Athon | |
| 5,861,015 A | 1/1999 | Benja-Athon | |
| 5,861,016 A | 1/1999 | Swing | |
| 5,948,006 A | 9/1999 | Mann | |
| 5,957,951 A | 9/1999 | Cazaux et al. | |
| 6,016,451 A | 1/2000 | Sanchez-Rodarte | |
| 6,026,328 A * | 2/2000 | Peckham et al. | 607/48 |
| 6,200,265 B1 | 3/2001 | Walsh et al. | |
| 6,275,737 B1 | 8/2001 | Mann | |
| 6,338,347 B1 | 1/2002 | Chung | |
| 6,445,955 B1 * | 9/2002 | Michelson et al. | 607/46 |
| 6,607,500 B2 | 8/2003 | Da Silva et al. | |
| 6,622,037 B2 | 9/2003 | Kasano | |
| 6,687,538 B1 | 2/2004 | Hrdlicka et al. | |
| 6,845,271 B2 | 1/2005 | Fang et al. | |
| 6,904,324 B2 | 6/2005 | Bishay | |
| 7,031,768 B2 | 4/2006 | Anderson et al. | |
| 2002/0019652 A1 | 2/2002 | Da Silva et al. | |
| 2002/0077572 A1 * | 6/2002 | Fang et al. | 601/15 |
| 2003/0014088 A1 | 1/2003 | Fang et al. | |
| 2003/0028170 A1 | 2/2003 | Anderson et al. | |
| 2003/0032859 A1 | 2/2003 | Belson | |
| 2003/0065368 A1 * | 4/2003 | Van Der Hoeven | 607/48 |
| 2003/0074030 A1 | 4/2003 | Leyde et al. | |
| 2003/0078633 A1 | 4/2003 | Firlik et al. | |
| 2003/0120259 A1 * | 6/2003 | Mickley | 604/528 |
| 2003/0195599 A1 | 10/2003 | Bishay | |

FOREIGN PATENT DOCUMENTS

| | | |
|---|---|---|
| WO | WO00/07665 | 2/2000 |

OTHER PUBLICATIONS

NeuroControl Corporation, NeuroControl StIM System brochure, circa 2000.

* cited by examiner

PORTABLE ASSEMBLIES, SYSTEMS AND METHODS FOR PROVIDING FUNCTIONAL OR THERAPEUTIC NEUROMUSCULAR STIMULATION

RELATED APPLICATIONS

This application is a continuation-in-part of U.S. patent application Ser. No. 10/777,771, filed Feb. 12, 2004, now U.S. Pat. No. 7,120,499, and entitled "Portable Percutaneous Assemblies, Systems and Methods for Providing Highly Selective Functional or Therapeutic Neuromuscular Stimulation," which is incorporated herein by reference. This application also claims the benefit of U.S. Provisional Patent Application Ser. No. 60/551,945, filed Mar. 10, 2004, and entitled "Steerable Introducer for a Percutaneous Electrode Usable in Association with Portable Percutaneous Assemblies, Systems and Methods for Providing Highly Selective Functional or Therapeutic Neuromuscular Stimulation," which is incorporated herein by reference. This application also claims the benefit of U.S. Provisional Patent Application Ser. No. 60/599,193, filed Aug. 5, 2004, and entitled "Implantable Pulse Generator for Providing Functional and/or Therapeutic Stimulation of Muscles and/or Nerves" which is incorporated herein by reference.

STATEMENT REGARDING FEDERALLY SPONSORED RESEARCH

This invention was made with government support under grant no. 1R43AR052211-01 awarded by the National Institutes of Health, through the National Institute of Arthritis and Musculoskeletal and Skin Diseases. The Government has certain rights in the invention.

FIELD OF INVENTION

This invention relates to systems and methods for providing neuromuscular stimulation.

BACKGROUND OF THE INVENTION

Neuromuscular stimulation can perform functional and/or therapeutic outcomes. While existing systems and methods can provide remarkable benefits to individuals requiring neuromuscular stimulation, many quality of life issues still remain. For example, existing systems perform a single, dedicated stimulation function. Furthermore, these controllers are, by today's standards, relatively large and awkward to manipulate and transport.

It is time that systems and methods for providing neuromuscular stimulation address not only specific prosthetic or therapeutic objections, but also address the quality of life of the individual requiring neuromuscular stimulation, including the ability to enable the end-user to operate the system through a wireless interface.

SUMMARY OF THE INVENTION

The invention provides improved assemblies, systems, and methods for providing prosthetic or therapeutic neuromuscular stimulation.

One aspect of the invention provides portable, percutaneous or surface mounted neuromuscular stimulation assemblies, systems and methods that provide electrical connections between muscles or nerves inside the body and stimulus generators or recording instruments temporarily mounted on the surface of the skin outside the body. The assemblies, systems, and methods may, in use, be coupled by percutaneous leads to electrodes, which are implanted below the skin surface, or, alternatively, may be coupled to conventional surface mounted electrodes, and positioned at a targeted tissue region or regions. The neuromuscular stimulation assemblies, systems, and methods apply highly selective patterns of neuromuscular stimulation only to the targeted region or regions, to achieve one or more highly selective therapeutic and/or diagnostic outcomes. The patterns can vary according to desired therapeutic and/or diagnostic objectives. The indications can include, e.g., the highly selective treatment of pain or muscle dysfunction, and/or the highly selective promotion of healing of tissue or bone, and/or the highly selective diagnosis of the effectiveness of a prospective functional electrical stimulation treatment by a future, permanently implanted device. In addition, the controller interface from the user to the neuromuscular stimulation assemblies, systems, and methods may be wireless.

The neuromuscular stimulation assemblies, systems, and methods comprise a skin-worn patch or carrier. The carrier can be readily carried, e.g., by use of a pressure-sensitive adhesive, without discomfort and without affecting body image on an arm, a leg, or torso of an individual.

The carrier carries an electronics pod, which generates the desired electrical current patterns. The pod houses microprocessor-based, programmable circuitry that generates stimulus currents, time or sequence stimulation pulses, and logs and monitors usage. The electronics pod may be configured, if desired, to accept wireless RF based commands for both wireless programming and wireless patient control.

The electronics pod also includes an electrode connection region, to physically and electrically couple percutaneous electrode leads to the circuitry of the electronics pod or to the surface mounted electrodes.

The carrier further includes a power input bay, to receive a small, lightweight, primary cell battery, which can be released and replaced as prescribed. The battery provides power to the electronics pod.

It is contemplated that, in a typical regime prescribed using the neuromuscular stimulation assemblies, systems, and methods, an individual will be instructed to regularly remove and discard the battery (e.g., about once a day or once a week), replacing it with a fresh battery. This arrangement simplifies meeting the power demands of the electronics pod. The use of the neuromuscular stimulation assemblies, systems, and methods thereby parallels a normal, accustomed medication regime, with the battery being replaced at a prescribed frequency similar to an individual administering a medication regime in pill form.

The power input bay can also serve as a communication interface. The communication interface may be plugged into a mating communications interface on an external device, or may have a wireless interface to an external device. Through this link, a caregiver or clinician can individually program the operation of a given electronics pod. If need be, the caregiver or clinician can modulate various stimulus parameters in real time.

The assemblies, systems, and methods make possible many different outcomes, e.g., (i) acute pain relief through treatment of pain or muscle dysfunction via the application of electrical stimulation to muscles (or their enervating nerves) with compromised volitional control due to injury to the peripheral or central nervous system (e.g., limb trauma, stroke, central nervous system diseases, etc.); and/or (ii)

maintenance of muscle function and prevention of disuse atrophy through temporary stimulation to maintain muscle strength, mass, peripheral blood flow, etc., following a temporary disruption of function by disease or injury; and/or (iii) enhanced tissue and bone regeneration through the provision of small DC currents (or very low frequency AC currents) in bone or tissue to aid or speed healing of bone unions, tissue re-growth, etc; and/or (iv) treatment of pain or other conditions through the application of nerve stimulation to provide a neuro-modulation or inhibitory effect; and/or (v) post-surgical reconditioning to enhance muscle function and promote recovery of strength post-operatively; and/or (vi) anti-thrombosis therapy, e.g., by the stimulation of leg muscles to increase venous return of blood; and/or (vii) the treatment of osteoporosis by cyclic stimulation of muscles; and/or (viii) the short-term provision of electrical stimulation to evaluate the effectiveness of such treatment in advance of the implantation of a more permanent implant, for example, to evaluate whether a person having C5-6 tetraplegia has an innervated triceps muscle which could respond to treatment by electrical stimulation; and/or (ix) the short-term recording of biopotential signals generated in the body to aid in the diagnosis of medical conditions or in the assessment of the effectiveness of treatment methods; and/or (x) for functional benefits such as in the restoration of impaired or lost gait or upper extremity function.

Another aspect of the invention provides systems and methods for implanting a percutaneous electrode. The systems and methods provide a percutaneous electrode with an anchoring element to resist movement of the percutaneous electrode within tissue. The systems and methods insert the percutaneous electrode through skin and tissue housed within an introducer, which shields the anchoring element from contact with tissue. The systems and methods implant the percutaneous electrode while inserted within the introducer, to place the percutaneous electrode in a desired location within tissue, but without placing the anchoring element in contact with tissue. The systems and methods withdraw the introducer to place the anchoring element in contact with tissue, thereby resisting movement of the percutaneous electrode from the desired position.

Another aspect of the invention provides systems and methods for implanting a percutaneous electrode. The systems and methods provide an introducer that defines an interior lumen. The interior lumen is sized and configured to shield a percutaneous electrode from contact with tissue during advancement to a desired position within tissue. A distal tissue penetrating region on the introducer includes a material that can be selectively deflected to steer the body along a chosen path toward the desired position. A mechanism is coupled to the distal region for altering the deflection the distal region in response to manipulation of a remote actuator.

Other features and advantages of the inventions are set forth in the following specification and attached drawings.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENT

The various aspects of the invention will be described in connection with providing functional neuromuscular stimulation for prosthetic or therapeutic purposes. That is because the features and advantages that arise due to the invention are well suited to this purpose. Still, it should be appreciated that the various aspects of the invention can beapplied to achieve other objectives as well.

I. Neuromuscular Stimulation Assembly 10

A. Overview

Figure 1:
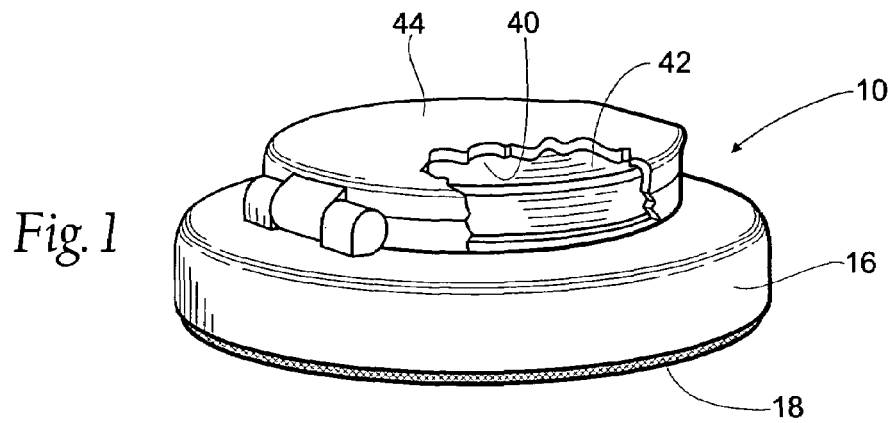
FIG. 1 is a perspective view of a neuromuscular stimulation assembly that provides electrical connections between muscles or nerves inside the body and stimulus generators temporarily mounted on the surface of the skin outside the body.
Figure 2:
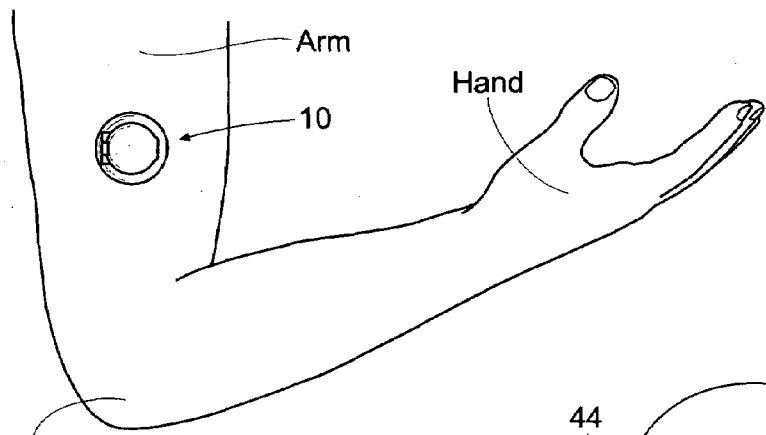
FIG. 2 is a view of the neuromuscular stimulation assembly shown in FIG. 1 worn on a temporary basis on an external skin surface of an arm.

FIG. 1 shows a neuromuscular stimulation assembly 10. As FIG. 2 shows, the neuromuscular stimulation assembly 10 is sized and configured so that, in use, it can be conveniently worn on a temporary basis on an external skin surface. By "temporary," it is meant that the presence of the neuromuscular stimulation assembly 10 can be well tolerated without discomfort for a period of time from several hours to a month or two, after which the neuromuscular stimulation assembly 10 can be removed and discarded.

Figure 3:
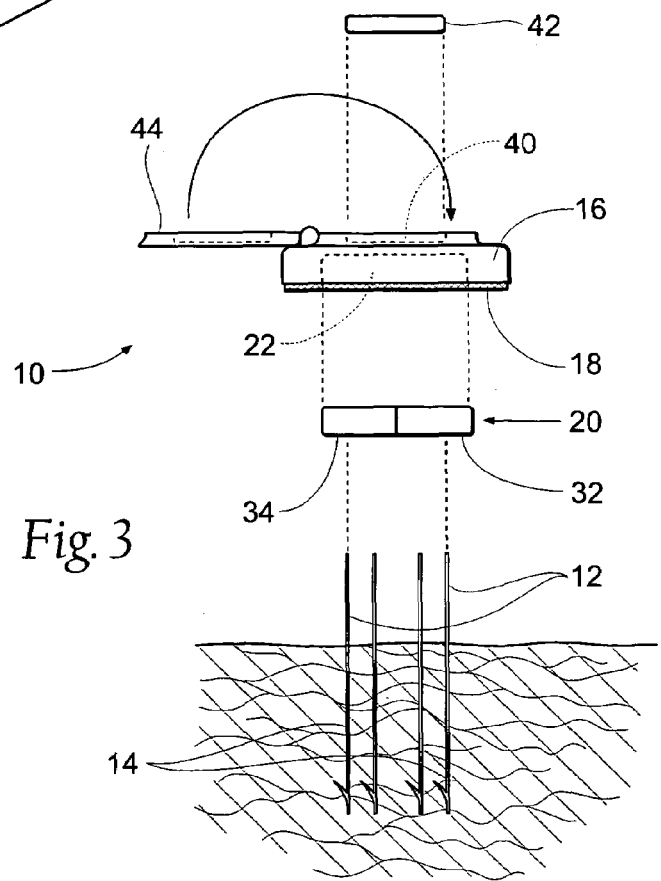
FIG. 3 is an exploded side view of the neuromuscular stimulation assembly shown in FIG. 1, showing its coupling to percutaneous leads to electrodes, which are implanted below the skin surface in a targeted tissue region or regions.

As FIG. 3 shows, the neuromuscular stimulation assembly 10 is, in use, releasably coupled by percutaneous leads 12 to electrodes 14, which are implanted below the skin surface in a targeted tissue region or regions. The tissue region or regions are targeted prior to implantation of the electrodes 14 due to their muscular and/or neural morphologies in light of desired therapeutic and/or functional and/or diagnostic objectives.

In use, the neuromuscular stimulation assembly 10 generates and distributes electrical current patterns through the percutaneous leads 12 to the electrodes 14. In this way, the neuromuscular stimulation assembly 10 applies highly selective patterns of neuromuscular stimulation only to the targeted region or regions, to achieve one or more highly selective therapeutic and/or diagnostic outcomes. As will be described in greater detail later, the inputs/stimulation parameters can vary according to desired therapeutic and/or diagnostic objectives. For example, the outcomes can comprise the highly selective treatment of pain or muscle dysfunction, and/or the highly selective promotion of healing of tissue or bone, and/or the highly selective diagnosis of the effectiveness of a prospective functional electrical stimulation treatment.

B. The Carrier

In its most basic form (see FIGS. 1 and 3) the neuromuscular stimulation assembly 10 comprises a patch or carrier 16. The carrier 16 desirably is sized and configured as a compact, lightweight housing made, e.g., of an inert, formed or machined plastic or metal material.

In a desired implementation, the carrier 16 approximates the geometry of the face of a wrist watch, measuring, e.g., about 1 inch in diameter, weighing, e.g., about 5 g. At this size, the carrier 16 can be readily worn without discomfort and in a cosmetically acceptable way (as FIG. 2 shows). The carrier 16 physically overlays and protects the site where the percutaneous electrode leads 12 pass through the skin.

Within its compact configuration, the carrier 16 includes several functional components, which will now be described.

C. The Adhesive Region

At least a portion of the undersurface of the carrier 16 (see FIGS. 1 and 3) includes an adhesive region 18. The function of the adhesive region 18 is to temporarily secure the carrier 16 to an external skin surface during use. For example, an inert, conventional pressure sensitive adhesive can be used. Desirably, the adhesive region contains a bacteriostatic sealant that prevents skin irritation or superficial infection, which could lead to premature removal.

Figure 19:
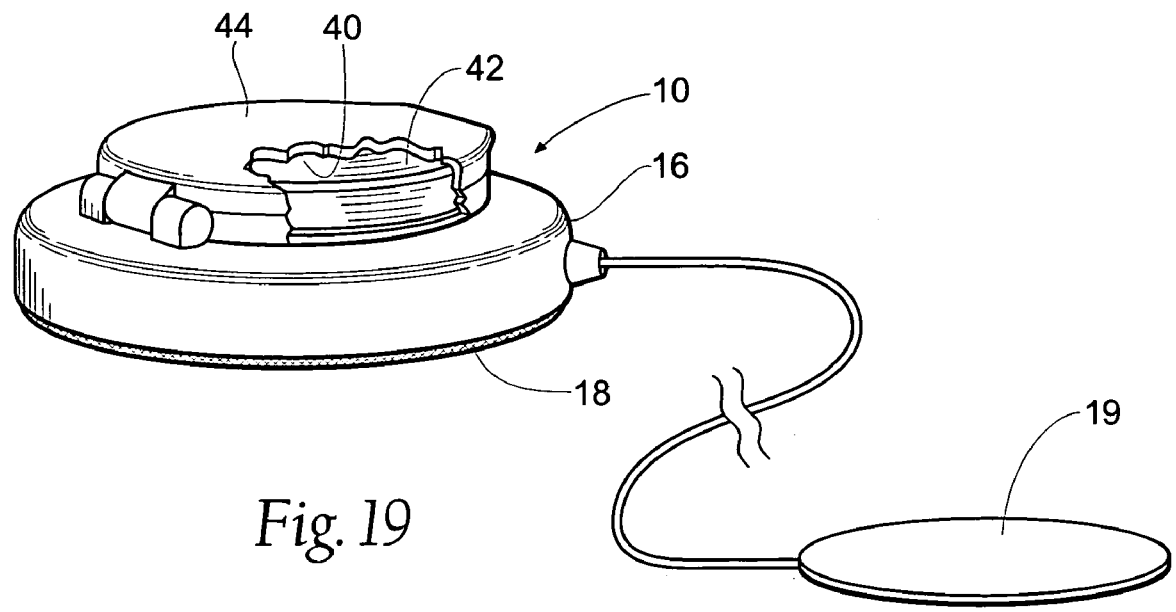
FIG. 19 is a perspective view of a neuromuscular stimulation system assembly of the type shown in FIG. 1, showing a secondary return electrode connected to the stimulation system.
Figure 20:
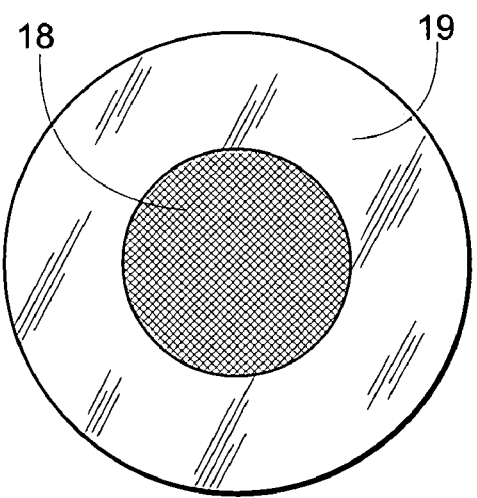
FIG. 20 is a bottom view of a neuromuscular stimulation system assembly of the type shown in FIG. 1, showing the adhesive region including both an active electrode portion and a return electrode portion.

The adhesive region 18 can also include an electrically conductive material. In this arrangement, the adhesive region 18 can serve as a return electrode, so that monopolar electrodes 14 can be implanted, if desired. The adhesive region 18 can also serve as an active electrode when it is used as a surface mounted stimulation system. In this configuration, a secondary return electrode 19 would be tethered to the stimulation system (see FIG. 19), or self contained within a concentric ring (see FIG. 20).

D. The Electronics Pod

The carrier 16 further carries an electronics pod 20, which generates the desired electrical current patterns and can communicate wirelessly with an external programming system or controller 46.

As FIG. 3 shows, the electronics pod 20 can comprise a component that can be inserted into and removed from an electronics bay 22 in the carrier 16. Having an electronics pod 20 that can be separated from the carrier 16 may be desired when the need to replace a carrier 16 during a course of treatment is necessary. For example, replacement of a carrier 16 without replacement of the electronics pod 20 may be desired if the anticipated length of use of the neuromuscular stimulation assembly 10 is going to be long enough to expect a degradation of adhesive properties of the adhesive region 18, or when the adhesive region 18 serves as a return electrode and may undergo, with use, degradation of adhesive properties and/or electrical conductivity.

Figure 12A:
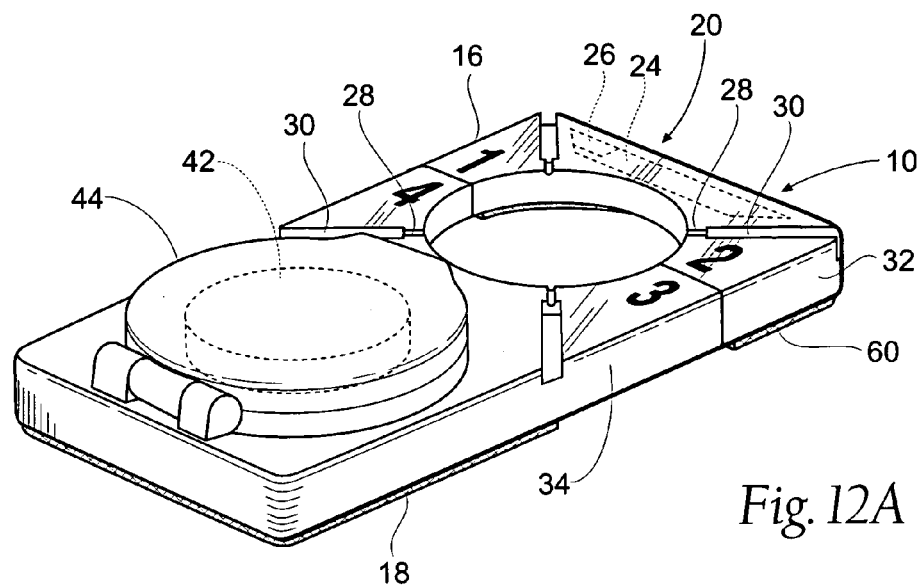
FIGS. 12A and 12B are perspective views of an alternative embodiment of a neuromuscular stimulation assembly, which includes an integrated electronics pod, with FIG. 12A showing the neuromuscular stimulation assembly in a closed condition for use, and FIG. 12B showing the neuromuscular stimulation assembly in an opened condition for receiving electrode leads prior to use.
Figure 12B:
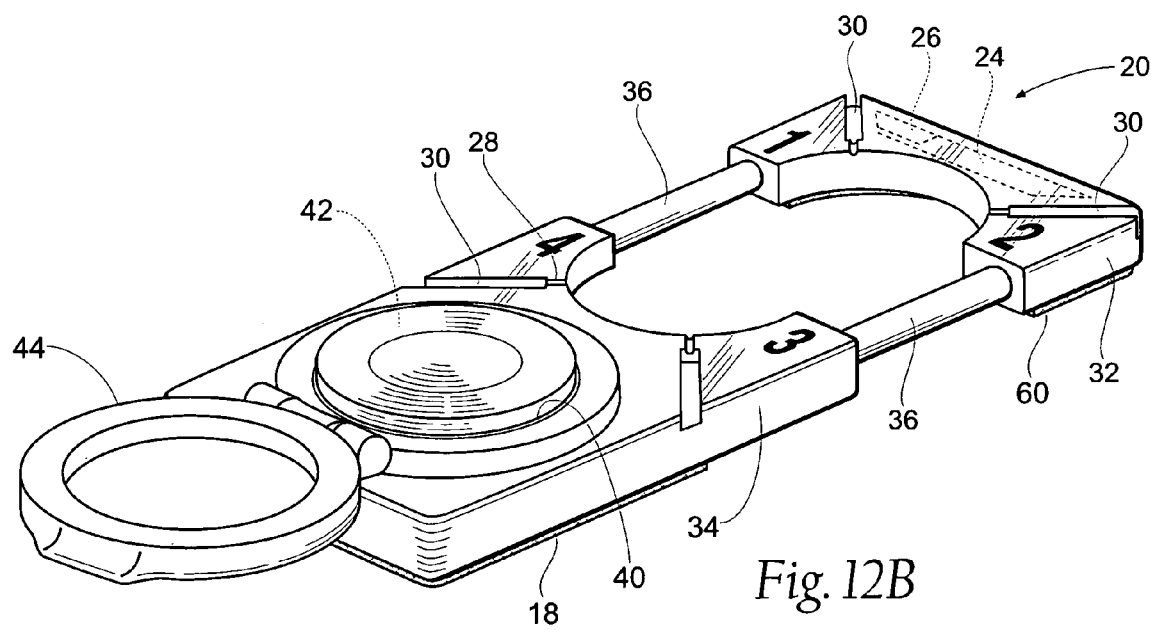

Alternatively, as FIGS. 12A and 12B show, the electronics pod 20 can comprise an integral, non-removable part of the carrier 16.

Regardless of whether the electronics pod 20 is removable from the carrier 16 (FIGS. 4A and 4B) or not (FIGS. 12A and 12B), the pod 20 houses microprocessor-based circuitry 24 that generates stimulus currents, time or sequence stimulation pulses, logs and monitors usage, and can communicate wirelessly through an RF link to an external programmer or controller. The circuitry 24 desirably includes a flash memory device or an EEPROM memory chip to carry embedded, programmable code 26. The code 26 expresses the pre-programmed rules or algorithms under which the stimulation timing and command signals are generated. The circuitry 24 can be carried in a single location or at various locations on the pod 20.

E. The Electrode Connection Region

Figure 4A:
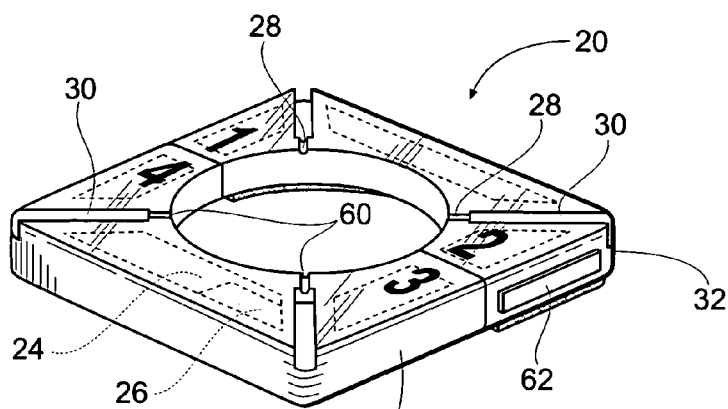
FIGS. 4A and 4B are perspective views of an electronics pod that is associated with the neuromuscular stimulation assembly shown in FIG. 1, which is capable of being docked within an electronics bay in the neuromuscular stimulation assembly for use, with FIG. 4A showing the pod in a closed condition for docking with neuromuscular stimulation assembly, and FIG. 4B showing the pod in an opened condition for receiving electrode leads prior to docking with the neuromuscular stimulation assembly.
Figure 10:
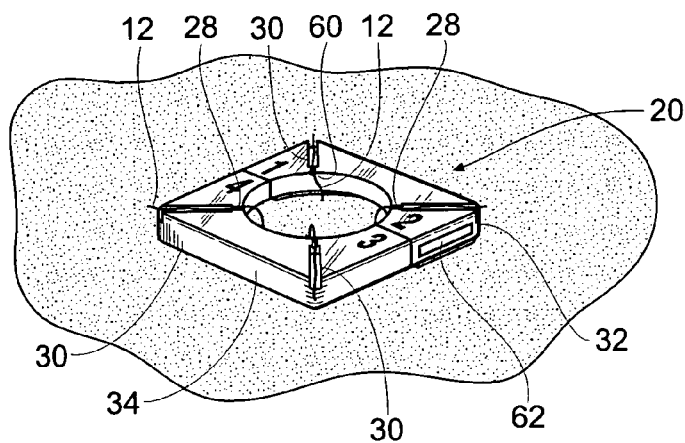
FIG. 10 shows the pod shown in FIG. 9, after having been placed in a closed condition, ready for use.

As FIGS. 4A/4B and FIGS. 12A/12B show, the electronics pod 20 also includes an electrode connection region 28. The function of the electrode connection region 28 is to physically and electrically couple the terminus of the percutaneous electrode leads 12 to the circuitry 24 of the electronics pod 20 (as FIG. 10 shows). The electrode connection region 28 distributes the electrical current patterns in channels—each electrode 14 comprising a channel—so that highly selective stimulation patterns can be applied through the electrodes 14. Four channels (numbered 1 to 4 on the pod 20) are shown in FIGS. 4A/4B and 12A/12B.

The electrode connection region 28 can be constructed in various ways. In the illustrated embodiments FIGS. 4A/4B and FIGS. 12A/12B), the electrode connection region 28 comprises troughs 30 formed in the electronics pod 20. Four troughs 30 are shown in FIGS. 4A/4B and FIGS. 12A/12B, each trough 30 being sized and configured to slidably receive the lead 12 of one electrode 12 in an interference fit (see FIG. 10). Each trough 30 is labeled with a number or other indicia to record the channel of the electronics circuitry 24 that is coupled to each trough 30.

Figure 7:
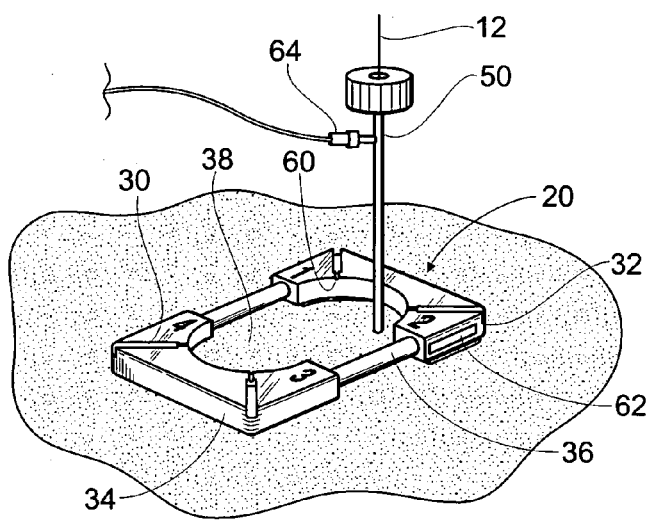
FIGS. 7 and 8 show the implantation of a first percutaneous electrode (FIG. 7) and the routing of its percutaneous electrode lead into an electrode connection region on pod (FIG. 8).

Each trough 30 routes the terminus of an electrode lead 12 to a given channel (see FIG. 7), allowing the lead 12 to be stretched taut to become frictionally lodged within the trough 30. In FIGS. 4A/4B, the trough 30 includes at its end a mechanism 60 to displace or pierce the insulation of the lead and make electrical contact with the conductive wire of the lead 12. This mechanically secures the lead 12 while electrically coupling the associated electrode 14 with the circuitry 24 of the electronics pod 20.

Figure 4B:
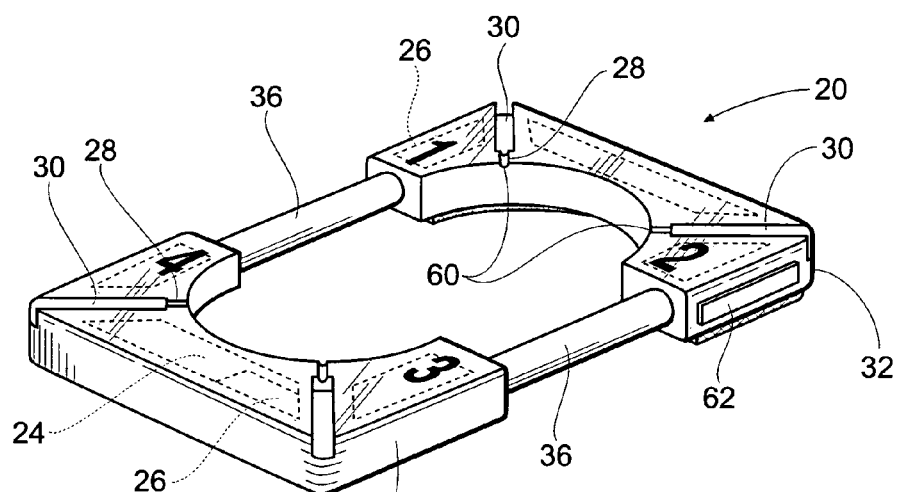

In the illustrated embodiment, for ease of installation, the electronics pod 20 shown in FIGS. 4A and 4B comprises mating left and right pod sections 32 and 34 joined in a sliding fashion by rails 36. The pod sections 32 and 34 can be separated by sliding apart along the rails 36 to an opened condition, as shown in FIG. 4B. The pod sections 32 and 34 can brought together by sliding along the rails 36 to a closed condition, as shown in FIG. 4A. The electronics circuitry 24 is carried within one or both of the pod sections 32 and 34.

Figure 8:
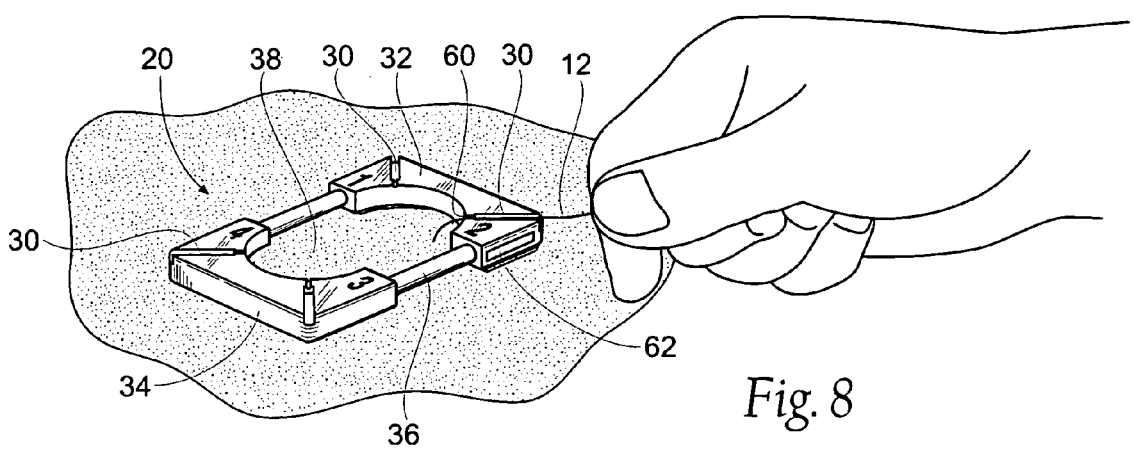
Figure 9:
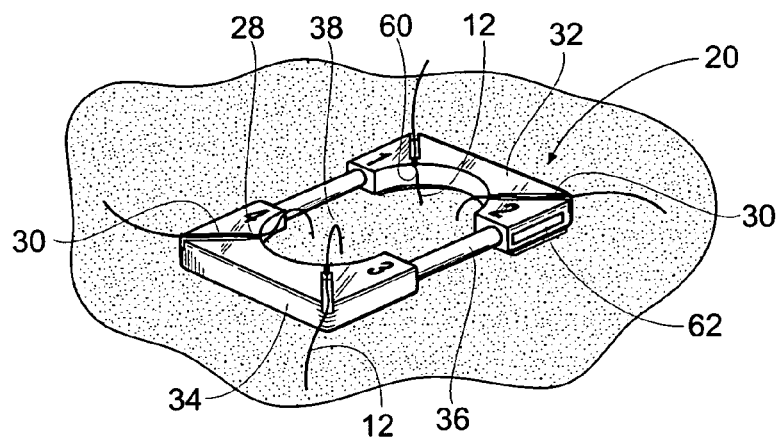
FIG. 9 shows the presence of second, third, and fourth percutaneous electrodes that have been sequentially implanted and the routing of their percutaneous electrode leads into the electrode connection regions on the pod, while the pod remains in the opened condition.

When in the opened position (see FIG. 6), the separated pod sections 32 and 34 expose a region 38 of underlying skin through which the electrodes 14 can be percutaneously implanted. The implantation of the electrodes 14 in this skin region 38 will be described in greater detail later. Opening of the pod sections 32 and 34 also makes the troughs 30 readily accessible for receipt and routing of the electrode leads 12 (see FIG. 8), which pass upward through the exposed skin region 38.

Figure 5:
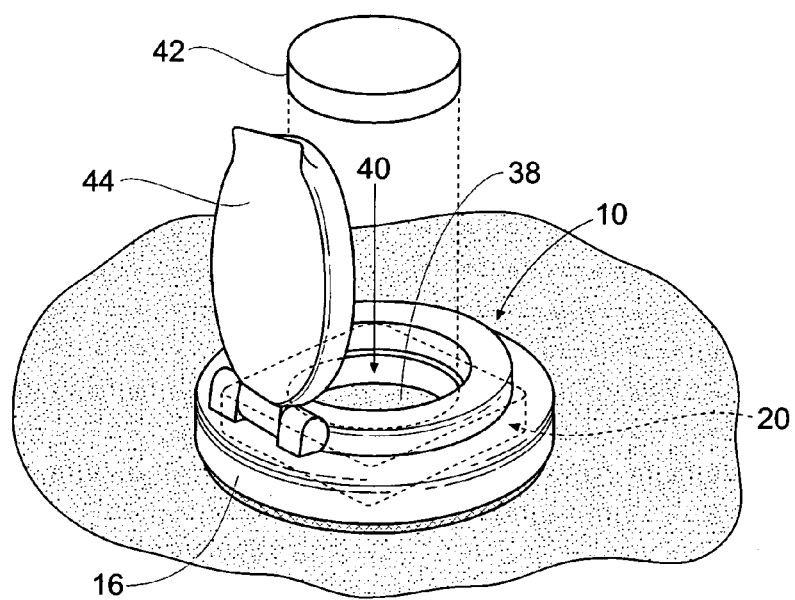
FIG. 5 is a perspective view of an electronics pod as shown in FIG. 4A docked within an electronics bay in a neuromuscular stimulation assembly for use, showing the power input bay opened and empty to enable visual inspection of underling skin.

Closing of the pod sections 32 and 34 (see FIG. 10), captures the electrode leads 12 within the mechanisms 60 in electrical connection with the circuitry 24 of the electronics pod 20. When in the closed condition (as FIG. 10 shows), the pod sections 32 and 34 mate but still allow visual inspection of the underlying skin region 38 through which the electrode leads 12 pass. As FIG. 5 shows, visual inspection of the underlying skin region 28 through the pod 20 is still accommodated even after the carrier 16 is docked to the pod 20 (by viewing through an empty power input bay 40 of the carrier 16).

Desirably, closing of the pod sections 32 and 34 also cuts off excess lead wire at the end. Otherwise, the excess lead can be cut manually. At this time (see FIG. 11), a carrier 16 can be placed over the electronics pod 20, by snap-fitting the electronics pod 20 into an electronics bay 22 of the carrier 16. An electrical connection region or contact 62 on the pod 20 electrically couples to a mating connection region or contact on the carrier 16, to couple the circuitry 24 on the pod 20 to a power source 42 carried by the carrier 16.

It should be appreciated that, in an arrangement where the electronics pod 20 is an integrated part of the carrier 16 (as shown in FIGS. 12A and 12B), the carrier 16 itself can comprise the separable sections 32 and 34. In this arrangement, one carrier section 34 can include an adhesive region 18, which will adhere the carrier 16 to the skin in an opened condition to allow routing of the electrode leads 12. Upon closing the carrier sections 32 and 34, a pull-away strip 60 on the other carrier section 32 can be removed to expose another adhesive region to entirely secure the carrier 16 to the skin.

Alternative embodiments are possible. For example, a locking motion, coupling the electrode leads 12 to the electronics pod 20, can be accomplished by a button, or a lever arm, or an allen drive that is pushed, or slid, or pulled, or twisted.

F. The Power Input/Communication Bay

Referring back to FIG. 3, the carrier 16 further includes a power input bay 40. One function of the power input bay 40 is to releasably receive an interchangeable, and (desirably) disposable battery 42, e.g., an alkaline or lithium battery. The battery 42 provides power to the electronics pod 20. If desired (see FIG. 3), the power input bay 40 can include a hinged cover 44. FIG. 12B also shows the presence of a battery-receiving power input bay 40. Alternatively, the battery 42 might form the cover without a hinge using a snap-fit mechanism to secure the battery into the power input bay 40.

It is contemplated that, in a typical regime prescribed using the neuromuscular stimulation assembly 10, an individual will be instructed to remove and discard the battery 42 about once a day, replacing it with a fresh battery 42. This arrangement simplifies meeting the power demands of the electronics pod 20. The use of the neuromuscular stimulation assembly 10 will thereby parallel a normal, accustomed medication regime, with the battery 42 being replaced in the same frequency an individual administers medication in pill form. The battery 42 may be provided in an over-molded housing to ease attachment and removal.

Figure 13A:
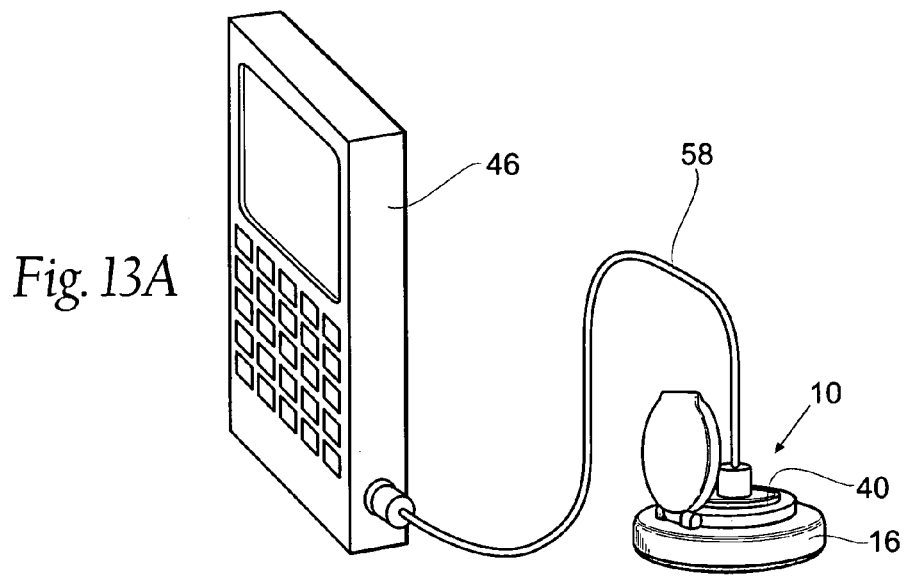
FIG. 13A is a perspective view of a neuromuscular stimulation assembly of the type shown in FIG. 1 coupled to an external programming instrument.

The power input bay 40 can also serve as a communication interface. As FIG. 13A shows, when free of a battery 42, the bay 40 can be used to plug in a cable 58 to an external programming device 46 or computer. This will also be described later. This makes possible linking of the electronics pod 20 to an external programming device 46 or computer. Through this link, information and programming input can be exchanged and data can be downloaded from the electronics pod 20.

In this way, the neuromuscular stimulation assembly 10 makes it possible for a care giver or clinician to individually program the operation of a given electronics pod 20 to the extent permitted by the embedded, programmable code 26. It should be appreciated, of course, that instead of using a cable interface, as shown, a wireless link 59 (e.g., RF magnetically coupled, infrared, or RF) could be used to place the electronics pod 20 in communication with an external programming device 46 or computer (see FIG. 13B).

As FIG. 5 also shows, with the battery 42 removed and the cover (if any) opened, the underlying skin region 38, through which the percutaneous electrode leads pass, can be readily viewed through the power input bay 40.

G. The Electrodes and their Implantation

Figure 14:
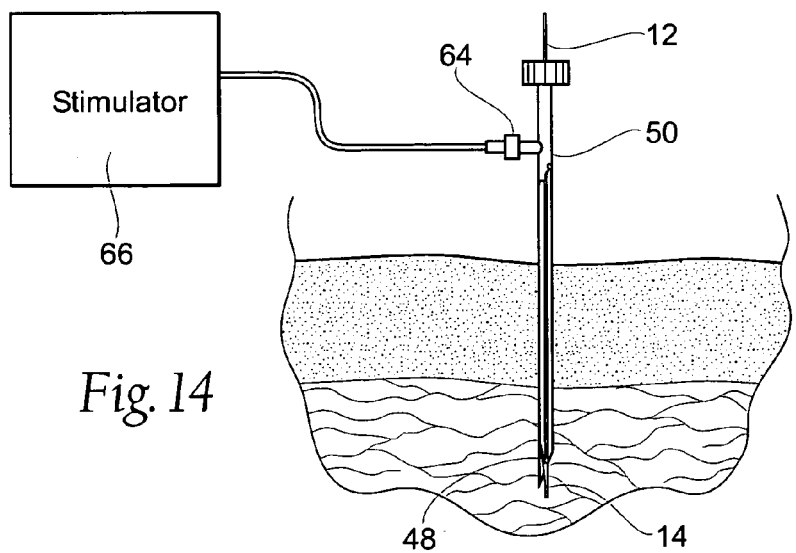
FIGS. 14 to 16 show the use of an electrode introducer to percutaneously implant an electrode in the manner shown in FIGS. 6 and 7 for connection to a neuromuscular stimulation assembly as shown in FIG. 11.

The configuration of the electrodes 14 and the manner in which they are implanted can vary. A representative embodiment will be described, with reference to FIGS. 14 to 16.

In the illustrated embodiment, each electrode 14 and lead 12 comprises a thin, flexible component made of a metal and/or polymer material. By "thin," it is contemplated that the electrode 14 should not be greater than about 0.5 mm (0.020 inch) in diameter.

The electrode 14 and lead 12 can comprise, e.g., one or more coiled metal wires with in an open or flexible elastomer core. The wire can be insulated, e.g., with a biocompatible polymer film, such as polyfluorocarbon, polyimide, or parylene. The electrode 14 and lead 12 are desirably coated with a textured, bacteriostatic material, which helps to stabilize the electrode in a way that still permits easy removal at a later date and increases tolerance.

The electrode 14 and lead 12 are electrically insulated everywhere except at one (monopolar), or two (bipolar), or three (tripolar) conduction locations near its distal tip. Each of the conduction locations is connected to a conductor that runs the length of the electrode and lead, proving electrical continuity from the conduction location to the electronics pod 20. The conduction location may comprise a de-insulated area of an otherwise insulated conductor that runs the length of an entirely insulated electrode. The de-insulated conduction region of the conductor can be formed differently, e.g., it can be wound with a different pitch, or wound with a larger or smaller diameter, or molded to a different dimension. The conduction location of the electrode may comprise a separate material (metal or conductive polymer) exposed to the body tissue to which the conductor of the wire is bonded.

The electrode 14 and lead 12 desirably possess mechanical properties in terms of flexibility and fatigue life that provide an operating life free of mechanical and/or electrical failure, taking into account the dynamics of the surrounding tissue (i.e., stretching, bending, pushing, pulling, crushing, etc.). The material of the electrode desirably discourages the in-growth of connective tissue along its length, so as not to inhibit its withdrawal at the end of its use. However, it may be desirable to encourage the in-growth of connective tissue at the distal tip of the electrode, to enhance its anchoring in tissue.

Figure 15:
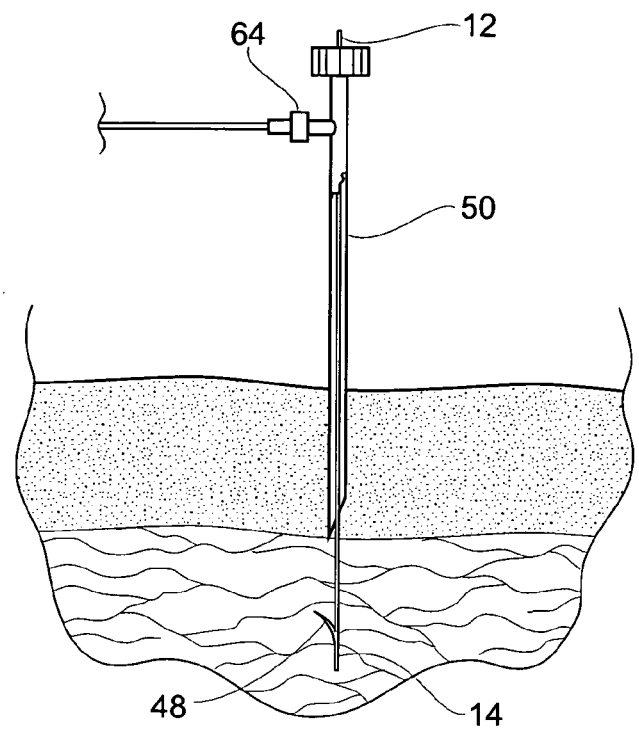
Figure 16:
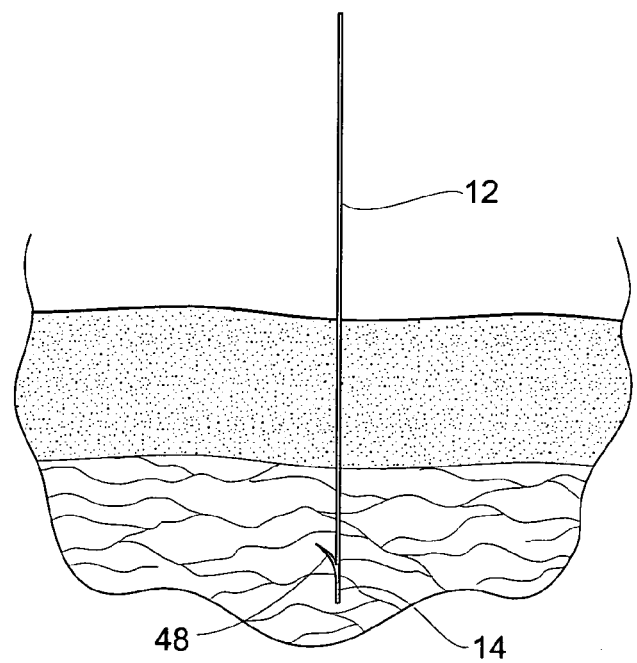

Furthermore, the desired electrode 14 will include at its distal tip, an anchoring element 48 (see FIGS. 15 and 16). In the illustrated embodiment, the anchoring element 48 takes the form of a simple barb. The anchoring element 48 is sized and configured so that, when in contact with tissue, it takes purchase in tissue, to resist dislodgement or migration of the electrode out of the correct location in the surrounding tissue. Desirably, the anchoring element 48 is prevented from fully engaging body tissue until after the electrode has been deployed. The electrode is not deployed until after it has been correctly located during the implantation (installation) process, as will be described in greater detail later.

In one embodiment, the electrode 14 and lead 12 can include a metal stylet within its core. Movement of the stylet with respect to the body of the electrode and/or an associated introducer (if used) is used to deploy the electrode by exposing the anchoring element 48 to body tissue. In this arrangement, the stylet is removed once the electrode 14 is located in the desired region.

In the illustrated embodiment (see FIGS. 14 and 15), each electrode 14 is percutaneously implanted housed within electrode introducer 50. The electrode introducer 50 comprises a shaft having sharpened needle-like distal tip, which penetrates skin and tissue leading to the targeted tissue region. The electrode 14 and lead 12 are loaded within a lumen in the introducer 50, with the anchoring element 48 shielded from full tissue contact within the shaft of the introducer 50 (see FIG. 14). In this way, the introducer can be freely manipulated in tissue in search of a desired final electrode implantation site (see FIG. 14) before deploying the electrode (see FIG. 15) and withdrawing the introducer 50 (see FIG. 16).

The electrode introducer 50 is insulated along the length of the shaft, except for those areas that correspond with the exposed conduction surfaces of the electrode 14 housed inside the introducer 50. These surfaces on the outside of the introducer 50 are electrically isolated from each other and from the shaft of the introducer 50. These surfaces are electrically connected to a connector 64 at the end of the introducer body (see FIGS. 14 and 15). This allows connection to a stimulating circuit 66 (see FIG. 14) during the implantation process. Applying stimulating current through the outside surfaces of the introducer 50 provides a close approximation to the response that the electrode 14 will provide when it is deployed at the current location of the introducer 50.

The electrode introducer 50 is sized and configured to be bent by hand prior to its insertion through the skin. This will allow the physician to place an electrode 14 in a location that is not in an unobstructed straight line with the insertion site. The construction and materials of the electrode introducer 50 allow bending without interfering with the deployment of the electrode 14 and withdrawal of the electrode introducer 50, leaving the electrode 14 in the tissue.

Figure 17A:
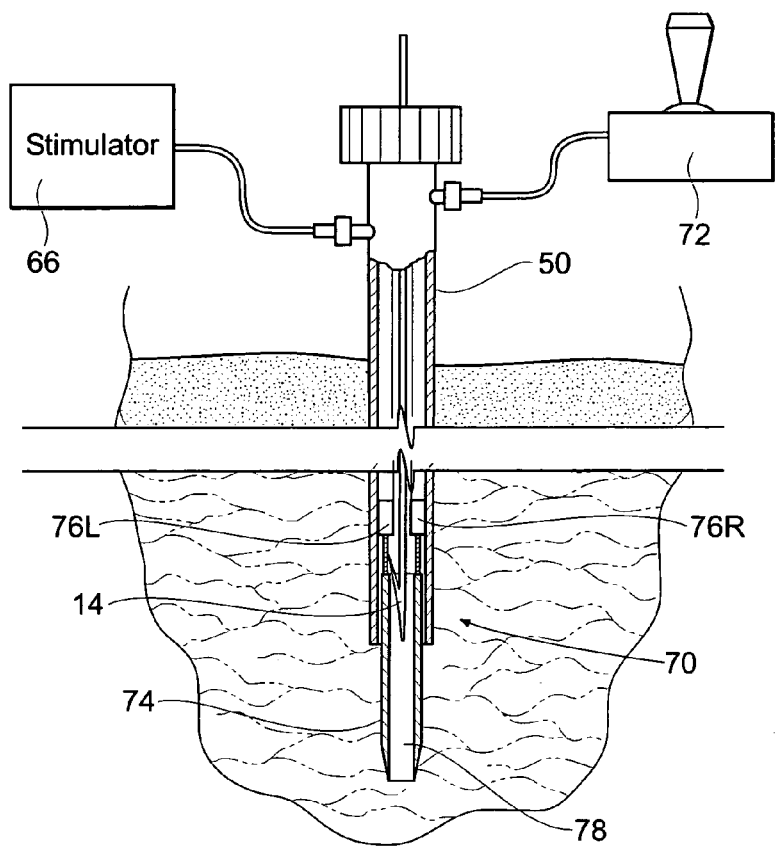
FIGS. 17A, 17B, and 17C show an electrode introducer having a remotely deflectable, distal needle region to percutaneously steer an electrode into a desired implant location prior to connection to a neuromuscular stimulation assembly as shown in FIG. 11.

In an alternative embodiment (see FIGS. 17A, 17B, and 17C), the electrode introducer 50 includes a distal needle region 70 that can be deflected or steered by operation of a remote steering actuator 72. Remote bending of the needle region 70 is another way to facilitate guidance of the electrode 14 to a location that is not in an unobstructed straight line with the insertion site.

The creation of the bendable needle region 70 that can be remotely deflected can accomplished in various ways. In the illustrated embodiment, the needle region 70 comprises a semi-flexible, electrically conductive, needle extension 74. The needle extension 74 is telescopically fitted within the distal end of the introducer 50, meaning that the extension 74 is capable of sliding within the introducer 50. The semi-flexible needle extension 74 includes an interior lumen 78, which communicates with the interior lumen of the introducer 50, through which the electrode 14 passes. Thus, the electrode 14 can be passed through the lumen 78 of the needle extension 74 for deployment.

Small linear motors 76L and 76R, e.g., employing conventional micro-electromechanical system (MEMS) technology, couple the proximal ends of the needle extension 74 to the introducer 50. The motors 76L and 76 are desirably attached in a spaced-apart relationship, which in the illustrated embodiment, is about 180-degrees.

Figure 17B:
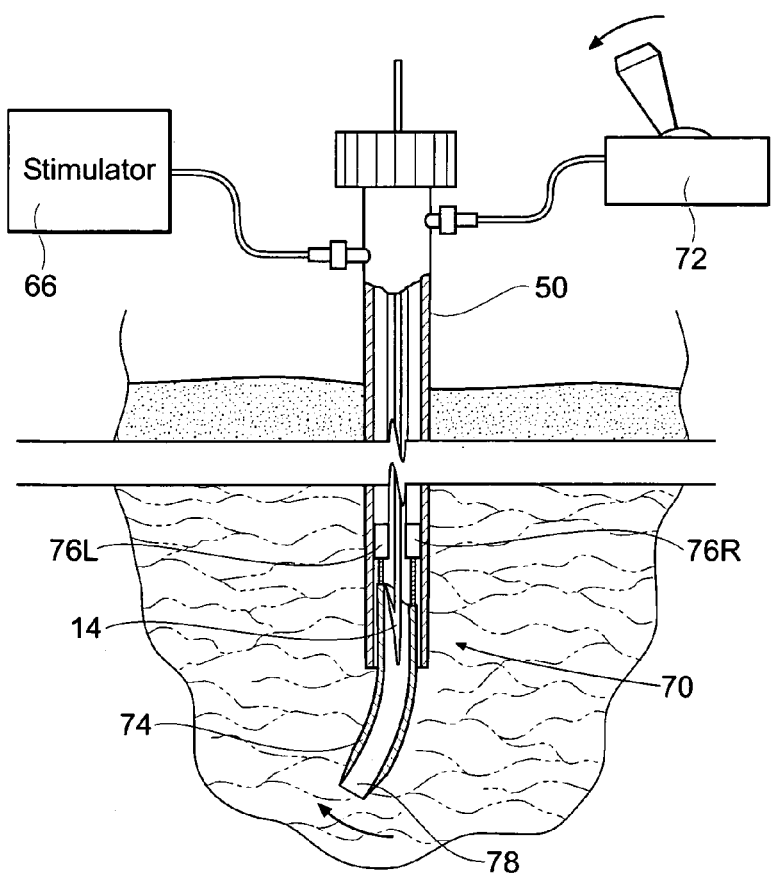
Figure 17C:
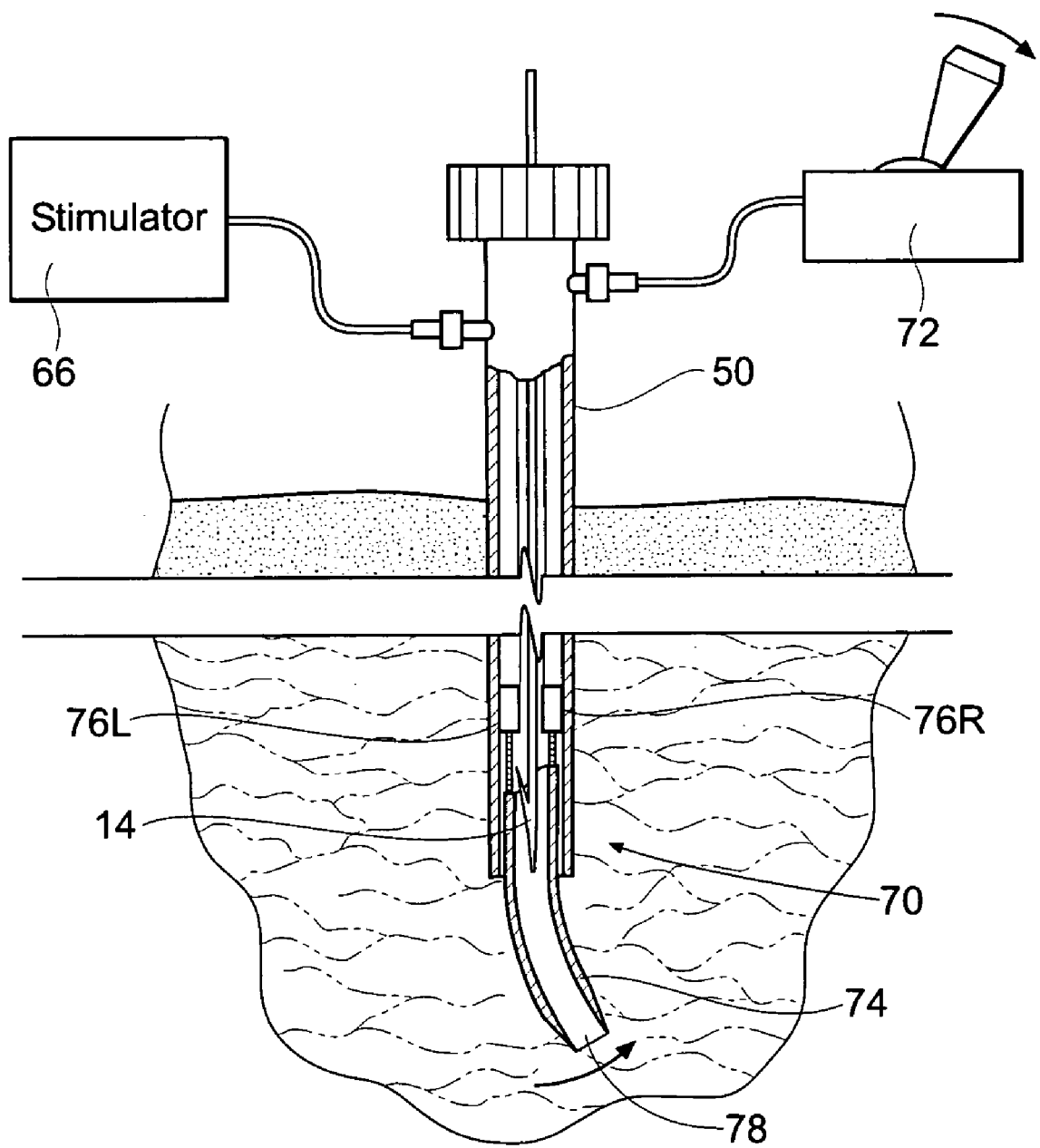

Driving the motors 76L and 76R at the same rate, forward or reverse, respectively extends or retracts the flexible extension 74 from the introducer 50 in a linear path. Driving the motors 76L and 76R at different rates, or in different directions, or both, imparts a bending torque on the needle extension 74, causing it to deflect. For example, driving the left side motor 76L at a faster forward rate than the right side motor 76R (or driving the left side motor 76L forward while driving the right side motor 76R in reverse) deflects the needle extension 74 to the right, as FIG. 17C shows. Conversely, driving the left side motor 76L at a slower rate than the right side motor 76R (or driving the right side motor 76R forward while driving the left side motor 76L in reverse) deflects the needle extension 74 to the left, as FIG. 17B shows.

In this arrangement, the steering actuator 72 can comprise, e.g., a conventional joystick device. By manipulating the joystick device 72, as FIGS. 17B and 17C show, variable drive rates/directions can be applied to the motors 76L and 76R, to deflect or steer the needle extension 74 in the desired direction. The path that introducer 50 takes through tissue can thereby be directed. While guiding the introducer 50 in this fashion, stimulating current can be applied through the outside surfaces of the needle extension 74 until the location having the desired stimulation response is found. The electrode 14 can be deployed through the needle extension 74, fully engaging the electrode anchoring element 48 in body tissue, in the manner previously described, followed by a withdrawal of the introducer 50.

Instead of MEMS linear motors 76L and 76R, conventional push-pull steering wires could be passed through lumens in the introducer 50 and coupled to the needle extension 74. Manipulation of the actuator 72 pushes or pulls on the wires to affect bending of the extension 74 in the manner just described.

II. Installation of the Neuromuscular Stimulation Assembly

Prior to installation, a clinician identifies a particular muscle and/or neural region to which a prescribed therapy using a neuromuscular stimulation assembly 10 will be applied. The particular types of therapy that are possible using the neuromuscular stimulation assembly 10 will be described later. Once the particular muscle and/or tissue region is identified, an electronics pod 20 (or a carrier 16 with integrated electronics pod 20) is placed on the skin overlying the region (see FIG. 6) and secured in place with pressure sensitive adhesive on the bottom of one-half of the pod/carrier. As previously stated, the adhesive region desirably contains a bacteriostatic sealant that prevents skin irritation or superficial infection, which could lead to premature removal.

Figure 6:
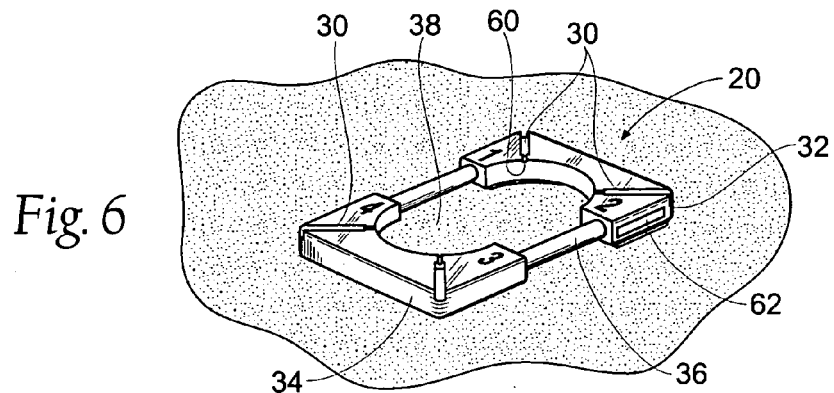
FIG. 6 is a perspective view of the electronics pod shown in FIG. 4B in an opened condition on a skin surface preliminary to placement of percutaneous electrodes.

As FIG. 6 shows, the electronics pod 20 (or carrier 16 with integrated electronics pod 20) is placed on the skin in an opened condition, to expose the skin region 38 between the pod (or carrier 16) sections 32 and 34.

As FIGS. 7 to 10 show, the clinician proceeds to percutaneously implant the electrodes 14 and lead 12, one by one, through the desired skin region 38. While each electrode 14 is sequentially implanted, the electrode introducer 50 applies a stimulation signal until a desired response is achieved, at which time the electrode 14 is deployed and the introducer 50 is withdrawn.

Upon implanting each electrode (see FIG. 7), the clinician routes each electrode lead 12 to a given trough 30. The clinician notes which electrode 14 is coupled to which channel.

Figure 11:
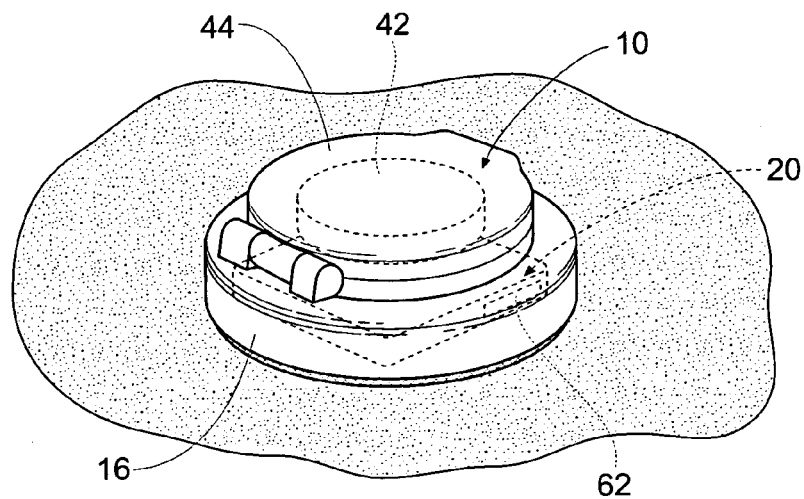
FIG. 11 shows the pod shown in FIG. 10, after having been docked within an electronics bay in the neuromuscular stimulation assembly for use.

After implanting all the electrode 14 and routing each lead 12 (see FIG. 9), the clinician closes the electronics pod 20 (or carrier 16 with integrated electronics pod 20) (see FIG. 10). In the former situation, the clinician snap-fits the carrier 16 over the electronics pod 20, as FIG. 11 shows. The adhesive region 18 on the carrier 16 secures the carrier 16 to the skin. A battery 42 is placed into the power input bay 40. The neuromuscular stimulation assembly 10 is ready for use.

Figure 18:
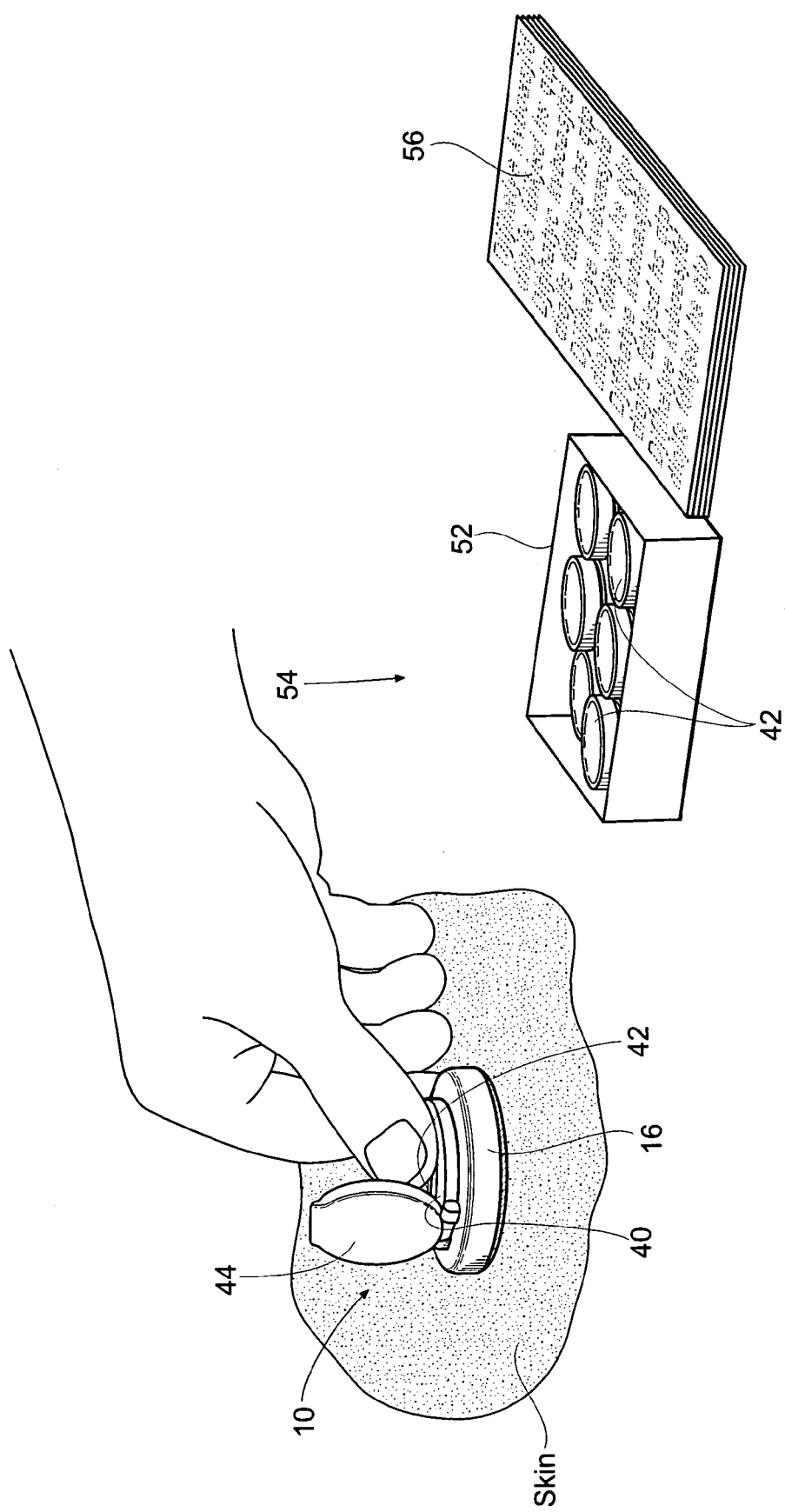
FIG. 18 is a perspective view of a neuromuscular stimulation system comprising a neuromuscular stimulation assembly of the type shown in FIG. 1 in association with a prescribed supply of replacement batteries and instructions for using the a neuromuscular stimulation assembly, including the recharging of the neuromuscular stimulation therapy by inserting a fresh battery, just as an individual on a medication regime "recharges" their medication therapy by taking a pill.

Typically, as shown in FIG. 18, a container 52 holding a prescribed number of replacement batteries 42 will be provided with the neuromuscular stimulation assembly 10, forming a neuromuscular stimulation system 54. Instructions for use 56 may accompany the neuromuscular stimulation system 54. The instructions 56 prescribe use of the neuromuscular stimulation assembly 10, including the periodic removal and replacement of a battery 42 with a fresh battery 42. Thus, the instructions 56 prescribe a neuromuscular stimulation regime that includes a periodic recharging, via battery replacement, of the neuromuscular stimulation assembly 10 in the same fashion that pill-based medication regime directs periodic "recharging" of the medication by taking of a pill. In the context of the neuromuscular stimulation system 54, a battery 42 becomes the therapeutic equivalent of a pill (i.e., it is part of a user action taken to extend treatment).

Figure 13B:
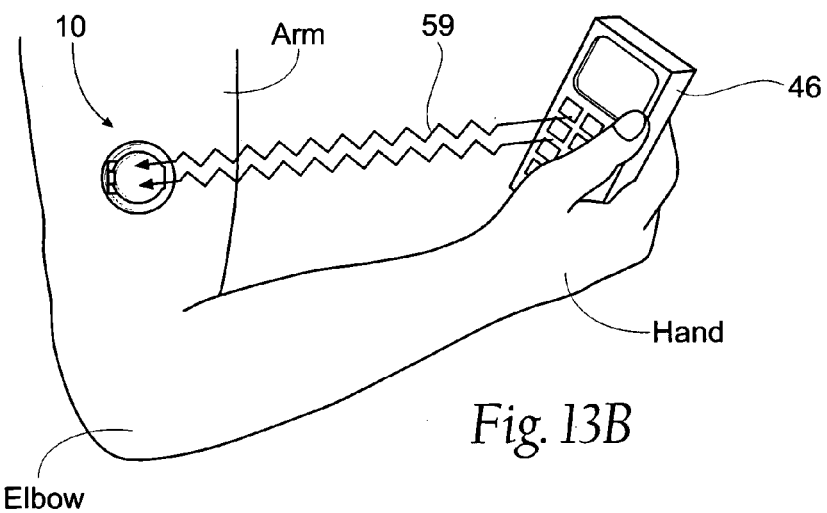
FIG. 13B is a perspective view of a neuromuscular stimulation assembly of the type shown in FIG. 1 in association with an external programming and control instrument that relies upon a wireless communication link.

As FIGS. 13A and 13B show, external desktop or handheld (desirably also battery powered) preprogrammed instruments 46 can be used to program stimulus regimes and parameters into the neuromuscular stimulation assembly 10, or to download recorded data from the neuromuscular stimulation assembly 10 for display and further processing. The instruments 46 can communicate with the neuromuscular stimulation assembly 10, e.g., by a cable connection 58, by radio frequency magnetic field coupling, by infrared, or by RF wireless 59. As before described, the power input bay 40 can additionally comprise a communications interface, that is coupled to a communications cable 58 connected to the instrument 46. The communications cable 58 provides power to the neuromuscular stimulation assembly 10 during programming, as well as communications with the circuitry 24 of the neuromuscular stimulation assembly 10. The external programming instrument 46 can also be a general purpose personal computer or personal digital device fitted with a suitable custom program and a suitable cable or interface box for connection to the communications cable 58.

The programming instruments 46 allow a clinician to customize the programmable code 26 residing in an individual neuromuscular stimulation assembly 10 according the specific needs of the user and the treatment goals of the clinician. The neuromuscular stimulation assembly 10 can, once customized, be disconnected from the programming system, allowing portable, skin-worn operation, as already described.

III. Representative Use of the Neuromuscular Stimulation Assembly/System

A. Overview

The neuromuscular stimulation assembly 10 and/or neuromuscular stimulation system 54, as described, make possible the providing of short-term therapy or diagnostic testing by providing electrical connections between muscles or nerves inside the body and stimulus generators or recording instruments mounted on the surface of the skin outside the body. The programmable code 26 of the neuromuscular stimulation assembly 10 and/or neuromuscular stimulation system 54 can be programmed to perform a host of neuromuscular stimulation functions, representative examples of which will be described for the purpose of illustration.

B. Continuous Active Motion (CAM)

CAM using the neuromuscular stimulation assembly 10 and/or neuromuscular stimulation system 54 provides the stimulus necessary to improve cardiovascular endurance, muscular strength, and neurologic coordination. Through the CAM, this active-assisted exercise is a technique used to assist the active, voluntary movement of the target limb, thereby decreasing the amount of strength needed to move the joints. This technique has been proven effective in increasing the strength of individuals beginning at very low levels. Therapeutic benefits include reduced inflammation of the affected joint, improved range of motion, pain relief, and enhanced functional mobility. CAM is differentiated from continuous passive motion (CPM), which is the movement of a joint or extremity through a range of motion without voluntary movement of the limb.

C. Post Trauma Anti-Scarring Treatment

Post Surgical scarring, (e.g. posterior approaches to the spine), is the bane of most Orthopedic or Neurosurgical procedures. Scarring or adhesion, that is a fibrous band of scar tissue that binds together normally separate anatomical structures during the healing process, can be one of the single greatest reasons for patient's surgical "failure". A terrific and well executed operation by a gifted surgeon can be wasted in a short time due to the body's tendency to scar during post surgical healing. By applying the neuromuscular stimulation assembly 10 and/or neuromuscular stimulation system 54 to the muscles or nerves in the specific surgical wound area, relatively small motions may prevent scarring, while the tissue is healing.

D. Temporary, Non-Surgical Diagnostic Assessment

Prior to the administering of a specific permanent implanted neuromodulation or neurostimulation system, (e.g. urinary incontinence, vagal nerve stimulation for epilepsy treatment, spinal cord stimulators for pain reduction), the neuromuscular stimulation assembly 10 and/or neuromuscular stimulation system 54 can be applied to provide the physician and their patient with some assurance that through the temporary stimulation of the end organ, the treatment is viable. This would allow the physician to screen patients that may not be candidates for the permanent treatment, or otherwise, may not find the effect of the treatment to worth the effort of the surgical implantation of a permanent system.

A specific example involves the treatment of C5-6 tetraplegics. C5-6 tetraplegics are unable to extend their elbow. Without elbow extension, they are limited to accessing only the area directly in front of their body, requiring assistance in many of their activities of daily living. They rely on the use of their biceps muscle to perform most of their upper extremity tasks. With limited or no hand function they rely on adaptive equipment to accomplish many self care activities such as grooming and hygiene as well as feeding.

An existing surgical procedure to restore elbow extension is to transfer a portion of the deltoid muscle into the triceps. This non-reversible surgical process requires extensive surgical intervention, prolonged post-operative immobilization and extended rehabilitation. Additionally, the timeframe to achieve a useful result post-operatively once the person recuperates from the surgery is no less than three months and may take up to a year to achieve full elbow extension.

As an alternative to the Deltoid to Triceps transfer, a pulse generator can be implanted in a minimal invasive way in association with a lead/electrode in electrical conductive contact with peripheral motor nerves that innervate the triceps muscle. The pulse generator can be programmed to provide single channel electrical stimulation to peripheral motor nerves that innervate the triceps muscle to produce elbow extension. Adding the ability to extend the elbow can significantly increase reach and work space thus allowing greater independence. With elbow extension, the ability to reach overhead or extend the arm outward to the side greatly increases this work space thereby allowing much more freedom to complete tasks otherwise out of their reach. This ability to extent also provides better control of objects as it provides, co-contraction of the elbow flexors and extensors simultaneously.

A first phase of treatment or evaluation period is desirably conducted to identify whether a person has an innervated triceps muscle which responds to electrical stimulation. If the muscle is innervated and functioning, the physician will identify if stimulation to this muscle can provide adequate elbow extension both in a horizontal plane such as reaching out and in a vertical plane for reaching up. The individual must also be able to overcome the force of this triceps stimulation with their biceps muscle by demonstrating that they can still flex their elbow during stimulation of the triceps. Usually this can be tested by asking the person to bring their hand to their mouth.

The evaluation process can be accomplished with a percutaneous or surface neuromuscular stimulation device of the type described herein. The stimulation device carries the on-board electronics pod, which generates the desired electrical current patterns to cause electrical stimulation of radial nerve innervation to the triceps. The pod houses microprocessor-based, programmable circuitry that generates stimulus currents, time or sequence stimulation pulses, and logs and monitors usage. As before described, a wireless user interface/programmer may be used.

If percutaneous electrodes are used, the circuitry of the electronics pod is physically and electrically coupled to the percutaneous leads of the electrodes. One week after placement of the percutaneous leads, the stimulator settings can be programmed, either by direct coupling or a wireless link to a programmer. Stimulation will be applied using 0-200 µsec pulses at 20 Hz. The force of triceps activation can be determined by the strength of their biceps muscle. The subject must maintain the ability to comfortably flex their elbow during triceps stimulation. A stronger biceps will allow for stronger stimulation to the triceps. The subject may require a conditioning phase of one to two weeks to build up the endurance of the triceps muscle following the initial set up. The subject must demonstrate the ability to flex the elbow while stimulation to the triceps is provided. Thus relaxation of biceps will allow elbow extension.

The individual will be scheduled for a second phase of treatment if electrical stimulation of the radial nerve innervation to the triceps using the surface or percutaneous stimulation program provides active elbow extension expanding the individual's previous work space.

The second phase of treatment includes the replacement of the first phase stimulation devices with the implantation of an implantable pulse generator and associated lead/electrode.

E. Neuroplasticity Therapy

Individuals with neurological deficits, such as stroke survivors or those with multiple sclerosis may lose control of certain bodily functions. The brain, may, through a process called "neuroplasticity," recover functionally, by reorganizing the cortical maps or spinal cord-root interfaces and increasing auxiliary blood supply, which contributes to neurological recovery. By applying the neuromuscular stimulation assembly 10 and/or neuromuscular stimulation system 54 to affected areas of the body and providing excitation and input to the brain, a neuroplastic effect may occur, enabling the brain to re-learn and regain control of the lost function.

F. Anti-Spasm Therapy

The use of temporary neurotoxins (e.g. botox) has become widespread in treating severe muscles spasms from cerebral palsy, head injury, multiple sclerosis, and spinal cord injury to help improve walking, positioning and daily activities. Botox can also be used to treat eye conditions that cause the eye to cross or eyelid to blink continuously. It is also purported to eliminate wrinkles by limiting the ageing process. The neuromuscular stimulation assembly 10 and/or neuromuscular stimulation system 54 may be used as an alternative means of reducing the spasticity without having to temporarily paralyze the nerves and muscles. The neuromuscular stimulation assembly 10 and/or neuromuscular stimulation system 54 also may be useful in treating TMJ (temporomandibular joint) disorders, which are manifested by pain in the area of the jaw and associated muscles spasms and limitations in the ability to make the normal movements of speech, facial expression, eating, chewing, and swallowing.

G. Chronic or Temporary Pain Therapy

Localized pain in any area of the body can be treated with the neuromuscular stimulation assembly 10 and/or neuromuscular stimulation system 54 by applying it directly to the effected area. The neuromuscular stimulation assembly 10 and/or neuromuscular stimulation system 54 works by interfering with or blocking pain signals from reaching the brain.

H. Post-Surgical Reconditioning

Recovery of strength and muscle function following surgery can be promoted using the neuromuscular stimulation assembly 10 and/or neuromuscular stimulation system 54. The assembly 10 and/or system 54 can be prescribed post-operatively and installed in association with the appropriate muscles regions to provide a temporary regime of muscle stimulation, alone or in conjunction with a program of active movements, to aid an individual in recovering muscle tone, function, and conditioning following surgery.

I. Thromboembolism Prophyllaxis

The neuromuscular stimulation assembly 10 and/or neuromuscular stimulation system 54 can provide anti-thrombosis therapy by stimulating the leg muscles which increases venous return and prevent blood clots associated with pooling of blood in the lower extremities. Routine post-operative therapy is currently the use of pneumatic compression cuffs that the patients wear on their calves while in bed. The cuffs cycle and mechanically compress the calf muscles, thereby stimulating venous flow. Patients hate this, but every surgical bed in the hospital now has this unit attached to it. This same effect could be duplicated by installing a neuromuscular stimulation assembly 10. Prophyllaxis is most effective if begun during surgery, as many, if not most clots, form during surgery. Thus, it is desirable to install a neuromuscular stimulation assembly 10 and begin use of the neuromuscular stimulation system 54 at the beginning of an operation.

J. Treatment of Osteoporosis

Cyclic muscle contraction loads bone sufficiently to prevent (and possibly) reverse osteoporosis. The effectiveness of such treatment is known to be frequency dependent. The neuromuscular stimulation assembly 10 and/or neuromuscular stimulation system 54 can be programmed to stimulate muscles at the appropriate frequency to prevent/reverse osteoporosis.

K. Neuroprosthesis

Restoration of lost motor due to a paralytic disease or injury can be achieved. The neuromuscular stimulation assembly 10 and/or neuromuscular stimulation system 54 can be wirelessly controlled in realtime through an external control source, such as a heel switch monitoring gait. This external control source would trigger the neuromuscular stimulation system to become active for a pre-set period of time, enabling a functional movement in the lower or upper extremity of a person, thereby restoring the previously non-functioning paralyzed limb.

L. Body Sculpting

Muscular proportions of the human anatomy can be enhanced and their overall muscle definition may be modified by neuromuscular stimulation of a specific group of muscles. An example is stimulation of the abdominal region, increasing strength and improving muscle tone and definition. The neuromuscular stimulation assembly 10 and/or neuromuscular stimulation system 54 can be programmed to stimulate muscles at the appropriate frequency to change body physique and supplement the impact of active exercise.

Various features of the invention are set forth in the following claims.

We claim:

1. A neuromuscular stimulation assembly comprising
a carrier sized and configured to be worn on the external skin surface, the carrier including a tissue facing surface,
at least one percutaneous electrode extending from the carrier,
circuitry carried on-board the carrier configured to generate a stimulation pulse to the electrode, and
the carrier tissue facing surface including a return electrode, the return electrode being coupled to the circuitry and in contact with the external skin surface.

2. An assembly according to claim 1
wherein the circuitry is removable from the carrier and replaceable.

3. An assembly according to claim 1
wherein the return electrode is a transcutaneous electrode.

4. An assembly according to claim 1
the carrier further including a power input bay sized and configured to hold a disposable battery for the circuitry that can be released and replaced for powering the circuitry,
instructions furnished by a clinician or caregiver or physician prescribing the release and replacement of the disposable battery according to a prescribed battery replacement regime, the prescribed battery replacement regime comprising the replacement of the disposable battery on a prescribed repeated basis similar to administering a pill under a prescribed pill-based medication regime, and
a supply of disposable batteries, each battery comprising a dose of power for the circuitry for administration according to the prescribed battery replacement regime.

5. A method of evaluating whether a person has an innervated muscle which responds to electrical stimulation comprising
providing a neuromuscular stimulation assembly comprising a carrier sized and configured to be worn on the external skin surface, the carrier including a tissue facing surface, at least one percutaneous electrode extending from the carrier, circuitry carried on-board the carrier configured to generate a stimulation pulse to the electrode, and the carrier tissue facing surface including a return electrode, the return electrode being coupled to the circuitry and in contact with the external skin surface,
placing the percutaneous electrode in association peripheral motor nerves that innervate the muscle,
placing the carrier on an external skin surface so the return electrode is in electrical contact with the external skin surface,
coupling the percutaneous electrode to the carrier, and
operating the circuitry to determine whether the person has an innervated muscle which responds to electrical stimulation.

6. A neuromuscular stimulation assembly comprising
at least one percutanous electrode sized and configured for stimulation of a targeted neural or muscular tissue region,
a carrier sized and configured to be worn on the external skin surface, the carrier including a tissue facing surface, programmable circuitry carried on-board the carrier configured to generate a stimulation pulse, the carrier tissue facing surface including a return electrode, the return electrode being coupled to the programmable circuitry and in contact with the external skin surface, a power input bay carried on-board the carrier that is electrically coupled to the circuitry, and an electrode connection element carried on-board the carrier that is electrically coupled to the circuitry, the electrode connection element being sized and configured to electrically couple the at least one electrode to the circuitry to apply the stimulation pulse to the tissue region.

7. An assembly according to claim 6 wherein the return electrode is a surface mounted return electrode.

8. An assembly according to claim 6 further including a communication bay carried on-board the carrier that is electrically coupled to the programmable circuitry, the communication bay being sized and configured to establish a wireless communication link between the circuitry and an external device.

9. An assembly according to claim 6 wherein the programmable circuitry is removable from the carrier and replaceable.

10. An assembly according to claim 6 wherein the power input bay is sized and configured to hold a disposable battery for the circuitry that can be released and replaced for powering the circuitry, the assembly further including instructions furnished by a clinician or caregiver or physician prescribing the release and replacement of the disposable battery according to a prescribed battery replacement regime, the prescribed battery replacement regime comprising the replacement of the disposable battery on a prescribed repeated basis similar to administering a pill under a prescribed pill-based medication regime, and a supply of disposable batteries, each battery comprising a dose of power for the circuitry for administration according to the prescribed battery replacement regime.

11. An assembly according to claim 4 or 10 wherein the prescribed battery replacement regime comprises the replacement of the disposable battery repeated at least on about a daily basis.

12. An assembly according to claim 4 or 10 wherein the prescribed battery replacement regime comprises the replacement of the disposable battery repeated at least on about a weekly basis.

13. A method for providing a neuromuscular stimulation function comprising providing a neuromuscular stimulation assembly comprising a carrier sized and configured to be worn on the external skin surface, the carrier including a tissue facing surface and a power input bay, the power input bay being sized and configured to hold a disposable battery for the circuitry that can be released and replaced for powering the circuitry, at least one percutaneous electrode extending from the carrier, circuitry carried on-board the carrier configured to generate a stimulation pulse to the electrode, and the carrier tissue facing surface including a return electrode, the return electrode being coupled to the circuitry and in contact with the external skin surface, providing instructions furnished by a clinician or caregiver or physician prescribing the release and replacement of the disposable battery according to a prescribed battery replacement regime, the prescribed battery replacement regime comprising the replacement of the disposable battery on a prescribed repeated basis similar to administering a pill under a prescribed pill-based medication regime, and providing a supply of disposable batteries, each battery comprising a dose of power for the circuitry for administration according to the prescribed battery replacement regime.

14. A method according to claim 13 wherein the prescribed battery replacement regime comprises the replacement of the disposable battery repeated at least on about a daily basis.

15. A method according to claim 13 wherein the prescribed battery replacement regime comprises the replacement of the disposable battery repeated at least on about a weekly basis.

* * * * *